United States Patent
de Boer et al.

(10) Patent No.: US 6,424,165 B1
(45) Date of Patent: Jul. 23, 2002

(54) ELECTROSTATIC APPARATUS FOR MEASUREMENT OF MICROFRACTURE STRENGTH

(75) Inventors: Maarten de Boer; Fernando Bitsie, both of Albuquerque, NM (US); Brian D. Jensen, Ann Arbor, MI (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/665,980

(22) Filed: Sep. 20, 2000

(51) Int. Cl.[7] .................. G01R 31/02; E21B 4/00; G01M 7/00; H02N 10/00
(52) U.S. Cl. .................. 324/754; 324/755; 324/758; 324/759; 73/152.17; 73/12.01; 73/760; 310/307; 310/309
(58) Field of Search .................. 324/754, 755, 324/759, 758; 310/309, 307; 73/152.17, 12.01, 760

(56) References Cited

U.S. PATENT DOCUMENTS

| | | | | |
|---|---|---|---|---|
| 3,842,664 A | * | 10/1974 | Conway, Jr. | 73/760 |
| 5,620,931 A | * | 4/1997 | Tsang et al. | 438/50 |
| 5,808,781 A | * | 9/1998 | Arney et al. | 359/291 |
| 5,949,682 A | * | 9/1999 | Dickinson et al. | 364/468.28 |
| 5,959,376 A | * | 9/1999 | Allen | 310/40 MM |
| 6,118,534 A | * | 9/2000 | Miller | 356/345 |
| 6,133,670 A | * | 10/2000 | Rodgers et al. | 310/309 |
| 6,137,206 A | * | 10/2000 | Hill | 310/309 |
| 6,211,599 B1 | * | 9/2001 | Barnes et al. | 310/309 |
| 6,291,922 B1 | * | 9/2001 | Dhuler | 310/307 |
| 6,323,663 B1 | * | 11/2001 | Nakata et al. | 324/754 |

* cited by examiner

Primary Examiner—N. Le
Assistant Examiner—Wasseem H. Hamdan
(74) Attorney, Agent, or Firm—Brian W. Dodson

(57) ABSTRACT

A new class of materials testing apparatus has been invented. Particularly suited to the measurement of fracture and fatigue properties in the extremely strong materials encountered in microelectromechanical systems, material strains well in excess of 1% can be applied pseudostatically, dynamically, or repetitively by these testers. There are no other practical methods to determine these material properties routinely in a process environment, and few alternatives in any circumstances.

18 Claims, 5 Drawing Sheets

ELECTROSTATIC APPARATUS FOR MEASUREMENT OF MICROFRACTURE STRENGTH

GOVERNMENT RIGHTS

This invention was made with Government support under Contract DE-AC04-94AL85000 awarded by the U.S. Department of Energy. The Government has certain rights in the invention.

FIELD OF THE INVENTION

The present invention relates generally to force measurement instrumentation, and more particularly to instrumentation adaptable to the special challenges of micromechanical applications.

BACKGROUND OF THE INVENTION

The development of practical micromechanical devices which can be operated reliably and manufactured routinely and with high process yield is currently hampered by a virtual absence of standard diagnostic instrumentation. Such fundamental parameters as physical structure, displacement distance, spring constants, fracture strength, forces, and many others cannot at present be measured routinely. Relative values for such parameters can at times be inferred from operating voltage, measured capacitance, and the like, but such indirect estimates fail badly when absolute accuracy is needed.

Fracture and material fatigue are structural phenomena which limit the performance of micromechanical apparati. Fracture strength in particular appears to depend sensitively upon process variations. The ability to rapidly and conveniently measure the fracture behavior of micromechanical materials would greatly assist the design process, and also provide a useful process diagnostic.

On the micromechanical size scale (0.1 to 100 microns), most materials used or contemplated are quite strong by conventional standards. This is related to the relatively low level of structural defects present in thin films of most materials considered suitable for micromechanical applications, and to impediments to dislocation motion and multiplication presented by the size of micromechanical structures. Typical materials used or contemplated for use include polycrystalline silicon, silicon oxides, silicon nitride, crystalline silicon, metals such as aluminum, tungsten, and gold, amorphous and polycrystalline diamond, and so on.

Despite the high strengths typical of micromechanical materials, the fracture behavior is still limiting, owing too the huge material strains which can be encountered in microelectromechanical systems (MEMS). Operating strains as large as 0.01 can be found in MEMS devices. Induced strains of this magnitude interact strongly with any flaws, grain interfaces, and other imperfections in a structural material. As a result, apparently small changes in microstructure, as might result from normal process variations, can dramatically alter yield, fracture, and fatigue behavior. Direct measurement of such phenomena as a routine part of the fabrication process is therefore greatly to be desired.

The use of electrostatic forces to fracture a test MEMS element is of a beneficial approach, particularly if this test is to be routinely applied as a process diagnostic. MEMS devices often use electrostatic forces to drive their operation, and the similarity in the devices allows co-fabrication. Also, rather than having to attach any external mechanical elements for the fracture test, application of a voltage across a pair of terminals is sufficient. The result is a much simpler test to build and use. However, electrostatic forces are quite small, and previous techniques have not proven suitable for MEMS process diagnostics.

A common prior art approach is to apply a force to a cantilever beam, usually by mechanical transfer of an externally generated force, until the beam fractures. However, integral electrostatic drives do not provide sufficient force to produce such fracture. An external electrostatic actuator (e.g., an interdigitated electrostatic comb drive) can generate large enough forces, but such devices use an unacceptably large area on a process wafer to be used as a routine diagnostic.

An electrostatically driven resonance technique has been used to apply strain to a MEMS-like test structure. Near resonance conditions, the storage of vibrational energy within the test structure produces localized areas where the strain is much greater than would be applied statically by the same drive mechanism. The behavior of the resulting system, however, is complex and rather difficult to interpret. It also measures a fatigue failure condition, rather than a simple fracture condition, because the strain is applied at the resonance frequency. Finally, such devices have not been able to induce failure of the test structure without the prior introduction of a microcrack. The test thus gives no information about initiation of fracture, which is usually the limiting step in material failure.

Finally, for pure materials studies it is possible to create a series of MEMS test structures such that a high level of residual strain is induced by the fabrication process, the eventual result being fracture. However, large residual strains are incompatible with proper function of most MEMS devices. MEMS devices are quite sensitive to unexpected or inhomogeneous residual strains. As a result, even if residual strains can be well localized on a small testing device, the associated far-field induced stresses can easily be large enough to prevent proper MEMS device function elsewhere on the process wafer. Again, such procedures appear undesirable for MEMS process diagnostics.

Accordingly, there is a long-felt need for a micromechanical device which can measure absolute forces with reasonable accuracy. Ideally, such a device would be integrable with production microelectromechanical systems (MEMS), and could be calibrated independent of other MEMS devices. Further, interpreting the output of such a device would be simplified if the basic design required limited material strain for operation. Finally, real-time diagnostics for proper functioning of the device would be useful.

SUMMARY OF THE INVENTION

The invention is of a new class of instruments to measure fracture and fatigue properties of structural materials for micromechanical devices. Electrostatic forces applied normal to a rigidly mounted compliant testing membrane are therein converted into forces which stretch the membrane. A stress concentration structure which is part of the compliant testing membrane allows the static or repeated imposition of multi-GPa stresses on the material being tested, thereby making fracture and fatigue studies practical in the micromechanical size regime.

BRIEF DESCRIPTION OF THE DRAWINGS

FIG. 7.

DETAILED DESCRIPTION

Figure 1:
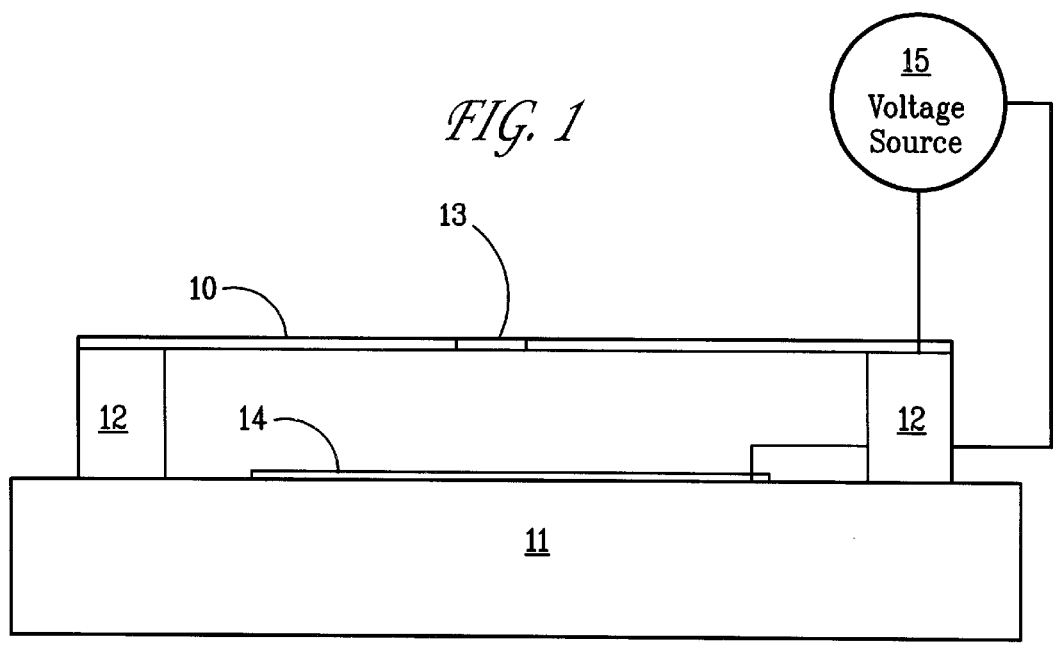
FIG. 1 Side view of an implementation of the instant invention.
Figure 2:
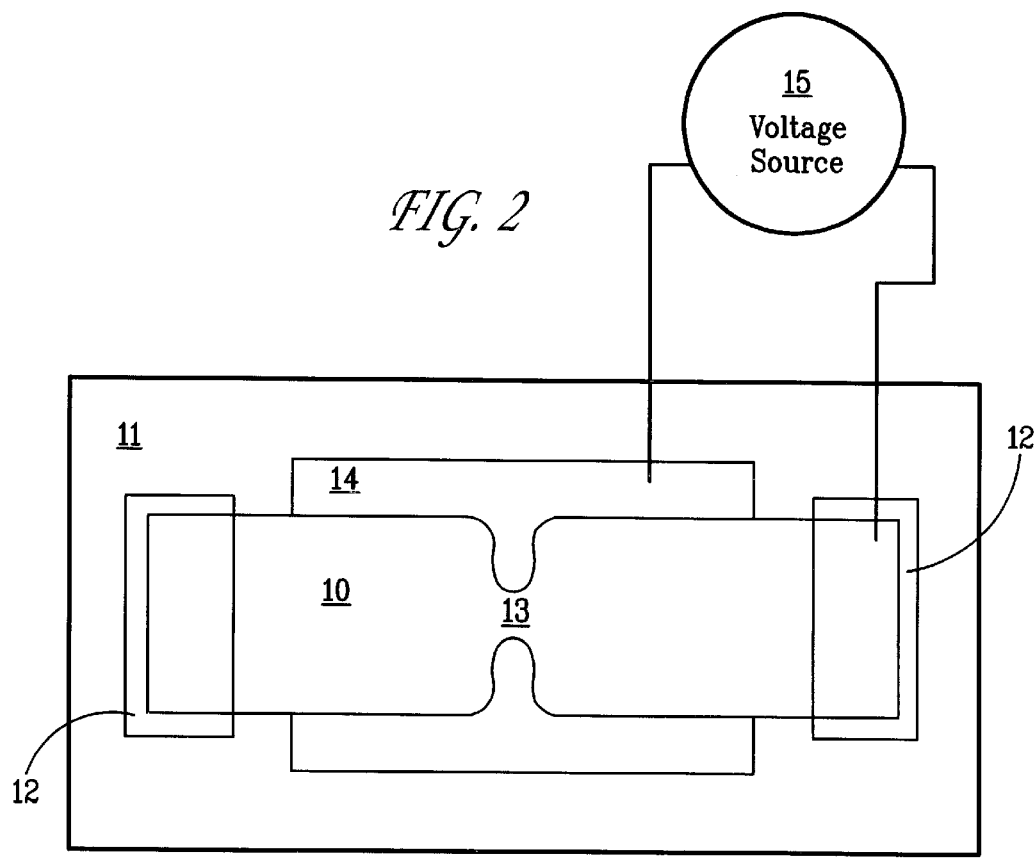
FIG. 2 Top view of an implementation of the instant invention.

A first implementation of the instant invention appears in a side view in FIG. 1, and in a top view in FIG. 2. Here the material to be tested is used to fabricate compliant testing membrane 10. Compliant testing membrane 10 is mounted above substrate 11 on rigid supports 12, said mounting carried out so that membrane 10 is essentially planar and parallel to the upper surface of substrate 11 in the absence of electrostatic forces. In this implementation, compliant testing membrane 10 is electrically conducting, and is insulated from substrate 11 by rigid supports 12, which in the present case are taken to be electrically insulating.

Compliant testing membrane 10 comprises a stress concentrating structure 13, which in this implementation is simply a lateral constriction in membrane 10 located in between the rigid supports 12. Finally, an electrical actuator pad 14 is located on the upper surface of substrate 11 under the compliant testing membrane 10. A voltage source 15 is functionally attached to the electrically conducting compliant testing membrane 10 and to the electrical actuator pad 14 so as to maintain a desired potential difference between these two structures.

Figure 3:
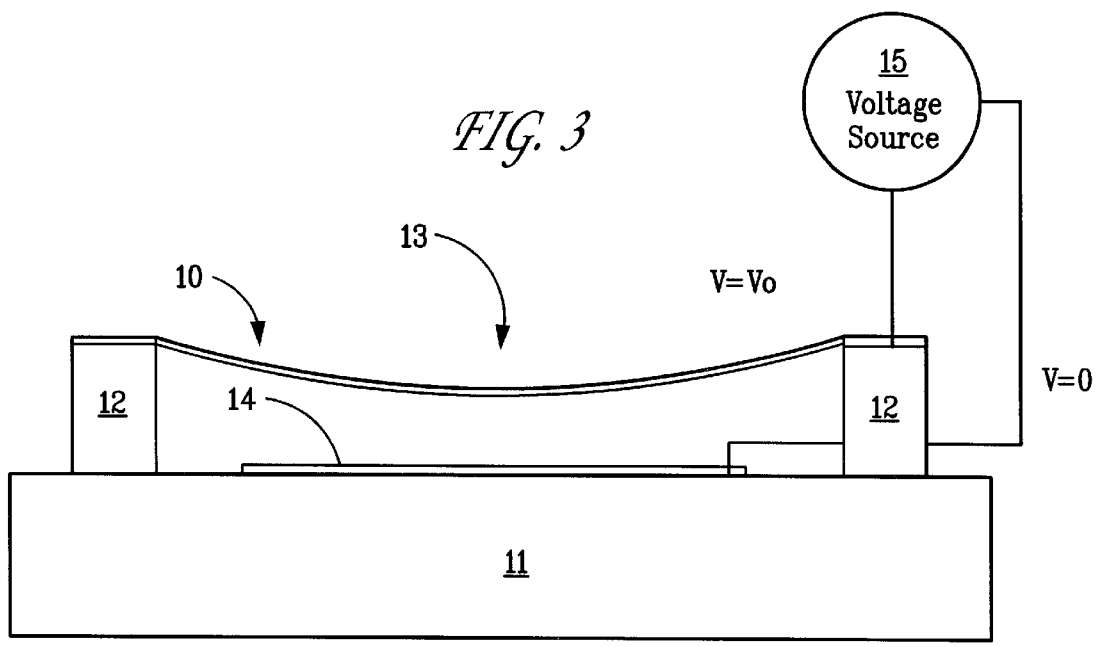
FIG. 3 Side view of an implementation of the instant invention in operation.

FIG. 3 shows the materials tester described above in action. A potential difference $V_o$ is maintained between membrane 10 and actuator pad 14 by the action of voltage source 15. This induces an electrostatic force F pulling the compliant testing membrane 10 and the actuator pad 14 toward each other. The rigid supports 12 and the substrate 11 form a rigid mounting system for the compliant testing membrane 10. As a result, the electrostatic force F deforms the compliant testing membrane 10, while the components of the rigid mounting system substantially remain in their V=0 positions.

The meaning of the terms "rigid" and "compliant", as used in this specification and in the claims, is important to establish. The testing membrane is mounted on the mounting system comprising the substrate and the rigid supports. A force is then applied which acts to draw the central portion of the membrane and the substrate surface closer together. In the extreme case where the mounting system is infinitely strong, the membrane mounts will not flex, and the stress energy generated by the membrane movement will all be localized within the testing membrane. In the other extreme case, where the membrane is much stronger than the mounting system, the stress energy will be localized within the mounting system, and the membrane cannot be subjected to significant levels of strain.

The extreme case of an infinitely strong mounting system, though very beneficial, cannot be attained when using real materials. A good approximation can, however, be achieved in practice. For example, in the implementation shown in FIG. 1, the testing membrane 10 has about 0.1 of the thickness of the rigid pillars 12. In such a structure most of the stress energy should be stored in mechanical strain of the testing membrane, if the mechanical properties of the membrane material and the materials of which the mounting system is fabricated are similar.

In this desirable situation, the mounting system will be called a rigid mounting system, and the testing membrane will be called a compliant testing membrane. Here "rigid"and "compliant"are terms which are only defined in view of the mechanical properties of the complete apparatus. That is, when the testing force is applied to the testing apparatus, the stress energy generated by the flexing of the apparatus is predominately stored in the stretching of the complaint testing membrane.

The effects of non-ideal rigidness and of non-ideal compliance can be modeled and quantitatively taken into account, but simplicity of analysis suggests that about 90% or more of the stress energy should be localized in the testing membrane for the testing membrane to be termed compliant, and for the mounting system to be termed rigid.

Given the dimensions of a typical MEMS device, a testing apparatus as shown in FIGS. 1 and 2 which does not have stress concentrating structure 13 will not be able to generate membrane strains greatly in excess of $10^{-3}$. Unfortunately, this value is well below common operating strain levels in some classes of MEMS devices, and far below the ultimate fracture strength of the materials used in such devices.

Introducing the stress concentrating structure 13 as shown in FIGS. 1 and 2, that is, a smooth pair of notches symmetric about both center lines of the testing membrane 10, allows much larger stresses to be attained in the central region of the constriction. This occurs for two reasons. First, the stress generated in the region of the constriction is amplified by the ratio of the width of the membrane and the width of the constriction (assuming that the testing membrane has constant thickness). Second, the total strain induced in the membrane by the applied testing force is preferentially localized in the region of the constriction.

The effect of any given stress concentrating structure can be accurately modeled up to the point of material failure by conventional mechanical design techniques. However, it is a significant simplification if the stress concentration structure is such that the deformation of the testing membrane with the stress concentrating structure remains essentially planar (i.e., so that regions do not curl up during testing), and such that no regions of highly localized and inhomogeneous material strain exist. Additional simplicity results if the electrostatic forces do not act directly upon the stress concentrating structure.

Figure 4:
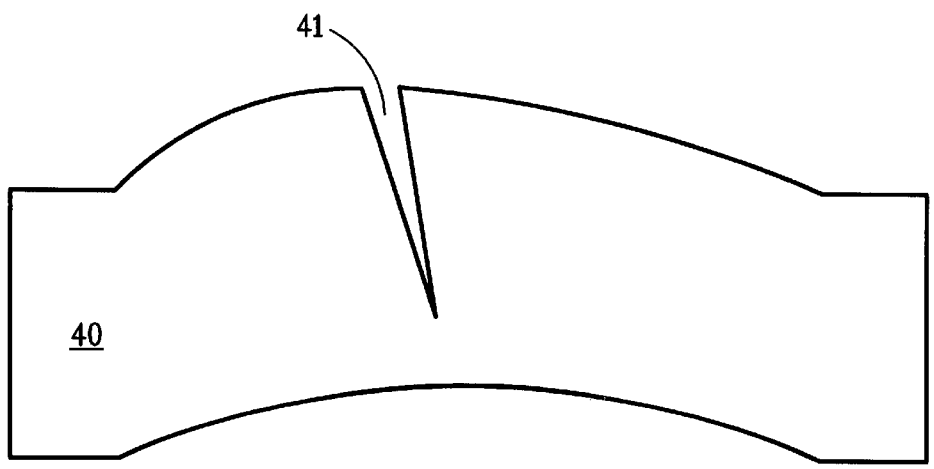
FIG. 4. Top view of a non-ideal compliant testing membrane.

An example of a testing membrane 40 comprising a stress concentrating structure 41 which would present difficulties for interpretation of the results of a testing apparatus after the present invention is shown in FIG. 4. If this testing membrane were mounted on the rigid mounting system shown in FIGS. 1 and 2, and the testing force applied, massive non-planar displacements are generated near the stress concentrating structure 41, while the stresses generated in the membrane are concentrated to tear the membrane at the sharp asymmetric point of the stress concentrating structure. Although in principle this apparatus could be used to measure ultimate mechanical properties, in practice better choices are available. Again, conventional use of modern material modeling techniques greatly aids the detailed design and data interpretation for this class of testing apparatus.

Figure 5A:
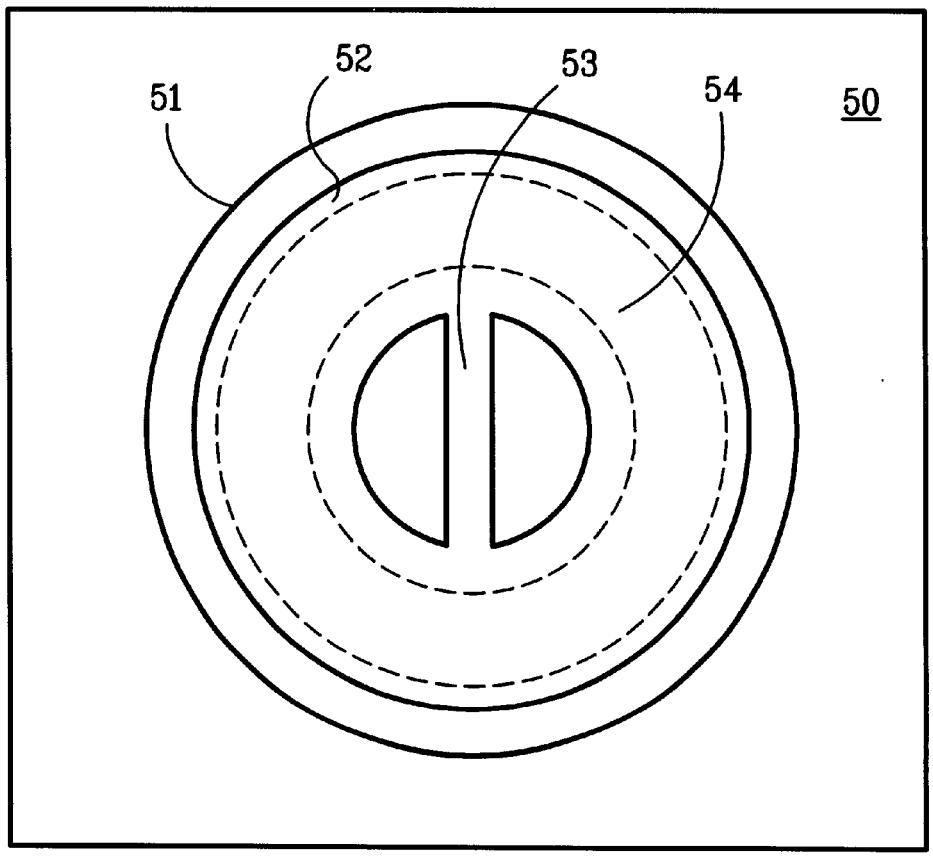
FIG. 5 Top (5a) and side (5b) of a circular testing apparatus after the instant invention.
Figure 5B:
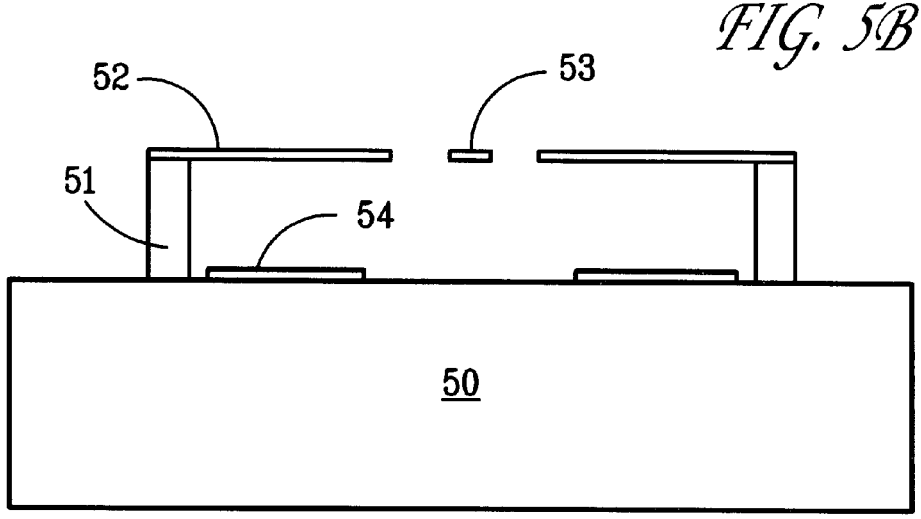

Another implementation of a testing apparatus after the instant invention is shown in a top view in FIG. 5a, and in a side center cross-section view in FIG. 5b. Here a mounting ring 51 is affixed on the upper surface of substrate 50. On top of mounting ring 51 is attached an electrically conducting circular testing membrane 52, which comprises stress concentrating structure 53, which here takes the form of a thin strip crossing a circular void in the center of the testing membrane 52.

The dimensions of substrate 50, mounting ring 51, and a testing membrane 52 are chosen so that the testing membrane is compliant, and the mounting system comprising substrate 50 and mounting ring 51 is rigid. An annular actuator electrode 54 is placed on the upper surface of the substrate under the testing membrane, such that it does not overlap the stress concentrating structure 53. When a voltage is applied between electrode 54 and testing membrane 52, a linear strain is generated in the stress concentrating structure 53.

Figure 6:
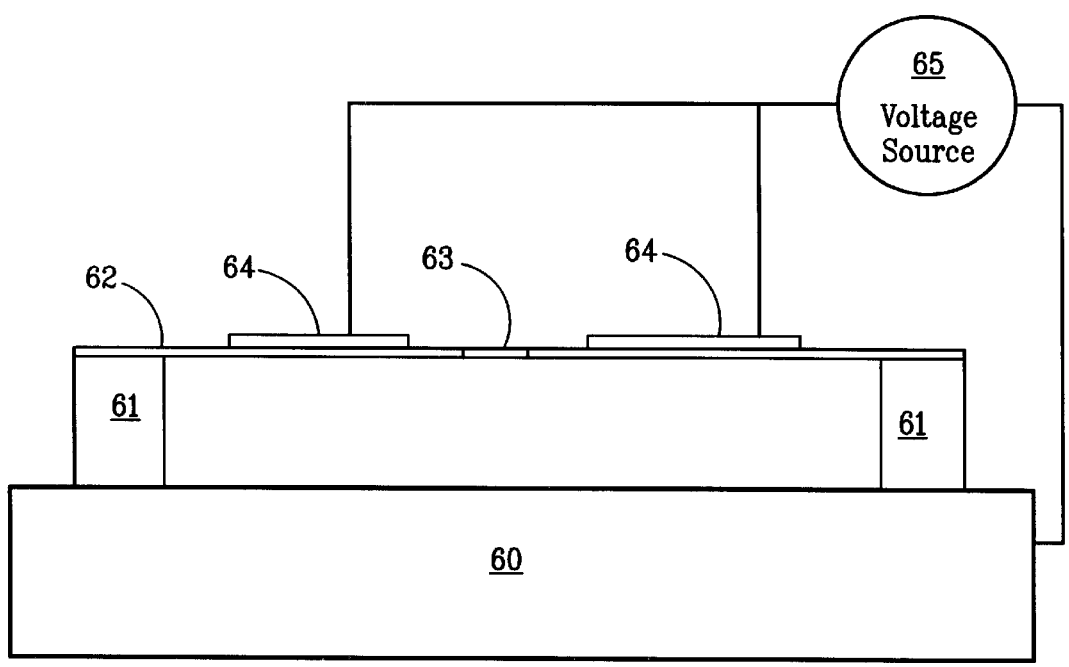
FIG. 6. Side view of an alternate implementation of a testing apparatus after the instant invention.

An alternate approach toward generating the electrostatic force is shown in FIG. 6. This is a testing apparatus quite similar to that shown in FIGS. 1 and 2. It comprises a substrate 60, a pair of rigid mounting pillars 61, a compliant testing membrane 62 comprising a stress concentrating structure 63, and a voltage source 65. However, in this case the substrate 60, or at least a layer near the upper surface of substrate 60, is electrically conducting, the compliant testing membrane 62 is not electrically conducting, and electrical actuator electrodes 64 are placed on membrane 62. Note that electrodes 64 can take the form of electrically conducting doped regions of membrane 62.

A different implementation exists where both the compliant testing membrane and the substrate are electrically conducting, and no actuator electrodes or pads are required for operation.

Having given several implementations of testing apparatus after the instant invention, it is necessary to describe how to collect the material information resulting from use of the testing apparatus. There are two types of changes in the condition of the apparatus which can be useful to measure, these being fracture and total failure of the testing membrane, and the deformation of the testing membrane prior to complete failure thereof. Between these two quantities, it is possible to measure elastic constants, plastic deformation, material fatigue, and material failure of the testing membrane under a wide range of loading conditions.

One of the simplest approaches, and the least intrusive on the testing process itself, is to monitor the state of the testing membrane optically. Deformations of the testing membrane can be measured interferometrically, and total failure of the testing membrane can be determined interferometrically or by direct imaging.

The state of the testing membrane can also be monitored using a variety of electrical probes. Failure of the testing membrane can be detected by monitoring the electrical continuity of the testing membrane, or by detecting development of an electrical short between the testing membrane and the substrate (or the associated electrical actuators. Deformation of the testing membrane can be determined with the help of a mechanical modeling program by measuring the capacitance between the testing membrane and the substrate surface. Such measuring techniques are well-known in the art.

Figure 7A:
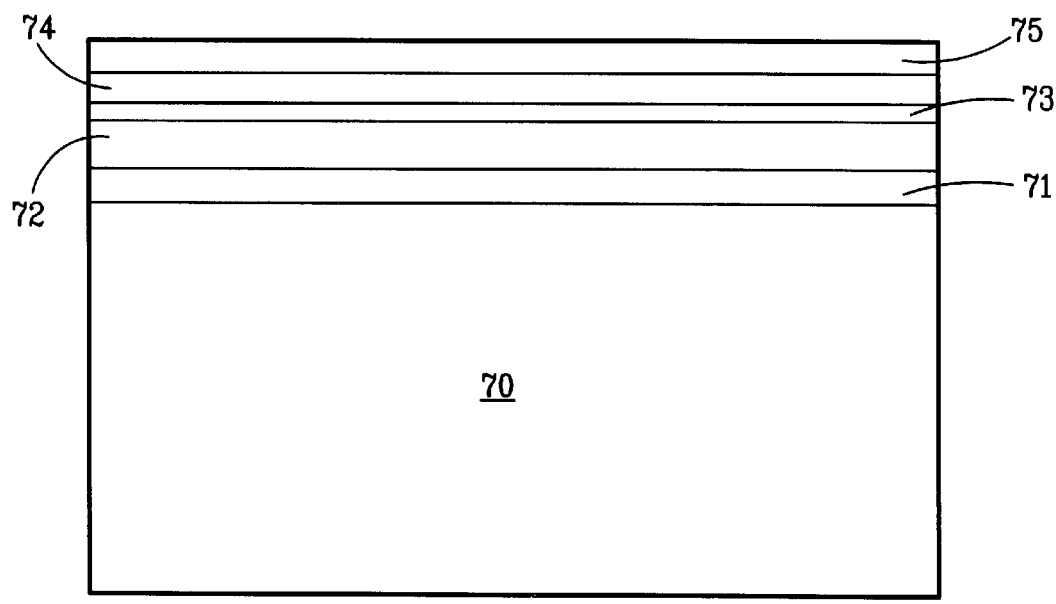
FIG. 7a shows a stack of structural layers as can be used for MEMS fabrication.

The particular suitability of testing apparatus after the instant invention can be seen by considering how most micromechanical devices are fabricated. As shown in FIG. 7a, a stack of structural and sacrificial layers of materials such as polysilicon (75), silicon oxides(71 and 74), silicon nitride (73), and silicon oxynitride (72) are sequentially deposited on a silicon substrate 70. Combined operations of patterning, preferential etching, and planarization allow fabrication of extremely complex MEMS devices.

Figure 7B:
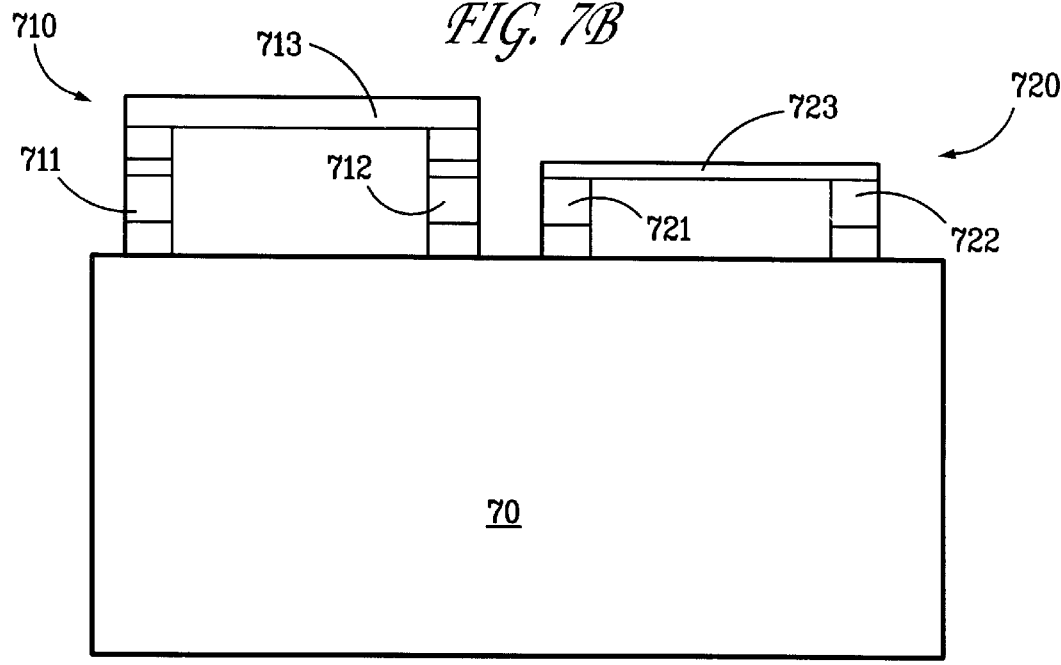
FIG. 7b shows a pair of testing apparati fabricated from that stack of layers.

These combined operations also make possible the fabrication of structures such as the testing apparatus shown in FIG. 7b. Here two testing apparati have been fabricated using the material layers defined in FIG. 7a, a first testing apparatus 710 to measure the properties of the polysilicon layer 75, and a second testing apparatus 720 to measure the properties of the silicon nitride layer 73.

The first testing apparatus 710 comprises substrate 70, the two four-layer rigid pillars 711 and 712, and compliant testing membrane 713, which is mounted atop rigid pillars 711 and 712, is suspended thereby over substrate 70, and is fabricated from polysilicon layer 75.

The second testing apparatus 720 comprises substrate 70, the two two-layer rigid pillars 721 and 722, and compliant testing membrane 723, which is mounted atop rigid pillars 721 and 722, is suspended thereby over substrate 70, and is fabricated from silicon nitride layer 73. The upper two layers are totally removed in constructing the second testing apparatus. Common MEMS fabrication techniques make forming the required electrodes and electrical connections a straightforward process.

The specific implementations described above are intended to teach various aspects of the instant invention, but are not intended to limit the scope of the invention being claimed. That scope is set by the claims in view of the specification.

What is claimed is:

1. An electrostatic testing apparatus, comprising:
    a) a compliant testing membrane comprising a stress concentrating structure;
    b) a rigid mounting system for said compliant testing membrane such that said membrane is supported on a principal plane in the absence of external forces, and,
    c) an electrostatic loading apparatus comprising a voltage source, such that said apparatus applies forces normal to said principal plane of the compliant testing membrane,
    wherein the rigid mounting system further comprises:
        a) a substrate with an upper surface;
        b) rigid supports mounted on said upper surface and supporting said compliant testing membrane, and
    wherein the electrostatic loading apparatus further comprises an electrical actuator pad on the substrate.

2. The apparatus of claim 1, wherein said compliant testing membrane has essentially constant thickness.

3. The apparatus of claim 1, wherein said compliant testing membrane consists essentially of a single thin film.

4. The apparatus of claim 1, such that the principal plane is parallel to said upper surface.

5. The apparatus of claim 1, wherein the electrostatic loading apparatus further comprises an electrically conducting upper surface of the substrate.

6. The apparatus of claim 1, wherein the electrostatic loading apparatus further comprises an electrically conducting compliant testing membrane.

7. The apparatus of claim 1, wherein the electrostatic loading apparatus further comprises an electrically conducting upper surface of the substrate, an electrically conducting compliant testing membrane, and electrically insulating rigid supports.

8. The apparatus of claim 1, wherein said electrical actuator electrode does not overlap the stress concentrating structure.

9. The apparatus of claim 1, wherein the electrostatic loading apparatus further comprises an electrical actuator pad on the upper surface of the substrate and an electrical actuator electrode on the compliant testing membrane.

10. The apparatus of claim 9, such that said electrical actuator pad does not extend under the stress concentrating structure.

11. The apparatus of claim 1, wherein the electrostatic loading apparatus further comprises an electrical actuator pad on the upper surface of the substrate and an electrical actuator electrode on the compliant testing membrane.

12. The apparatus of claim 1, wherein the electrostatic loading apparatus further comprises a plurality of electrical actuator pads on the upper surface of the substrate.

13. The apparatus of claim 12, wherein the electrostatic loading apparatus further comprises a plurality of electrical actuator electrodes on the compliant testing membrane.

14. The apparatus of claim 1, wherein the electrostatic loading apparatus further comprises a plurality of electrical actuator electrodes on the compliant testing membrane.

15. The apparatus of claim 1, wherein the voltage source allows repetitive activation of the electrostatic loading apparatus.

16. The apparatus of claim 1, wherein the compliant testing membrane is electrically conductive and the apparatus further comprises a electrical continuity fracture detector.

17. The apparatus of claim 1, further comprising optical apparatus to measure displacements of the complaint testing membrane from the principal plane.

18. The apparatus of claim 1, further comprising a meter to measure capacitance between the substrate and the compliant testing membrane.

* * * * *